United States Patent [19]

Lover et al.

[11] 4,215,116

[45] Jul. 29, 1980

[54] PROPOXYLATE TOXICANTS

[75] Inventors: Myron J. Lover, Mountainside; Arnold J. Singer, S. Orange; Donald M. Lynch, Waldwick, all of N.J.

[73] Assignee: Block Drug Company Inc., Jersey City, N.J.

[21] Appl. No.: 920,808

[22] Filed: Jun. 30, 1978

[51] Int. Cl.$^2$ .................. A01N 9/00; A01N 9/24; A01N 9/36

[52] U.S. Cl. .................. 424/217; 424/78; 424/307; 424/308; 424/342

[58] Field of Search .................. 424/342, 217

[56] References Cited

U.S. PATENT DOCUMENTS

| | | | |
|---|---|---|---|
| 2,861,887 | 11/1958 | Colby et al. | 424/342 |
| 3,033,889 | 5/1962 | Chiddix et al. | 260/461 |
| 3,122,478 | 2/1964 | Lafon | 424/342 |
| 3,291,580 | 12/1966 | Malich | 424/342 |
| 3,433,578 | 3/1969 | Reid | 424/342 |
| 3,888,994 | 6/1975 | Wagner et al. | 424/342 |
| 4,005,192 | 1/1977 | Graham et al. | 424/342 |
| 4,011,313 | 3/1977 | Thompson | 424/342 |

FOREIGN PATENT DOCUMENTS

| | | | |
|---|---|---|---|
| 1217558 | 2/1958 | France | 424/342 |
| 5176423 | 12/1974 | Japan | 424/342 |

*Primary Examiner*—Allen J. Robinson
*Attorney, Agent, or Firm*—Ostrolenk, Faber, Gerb & Soffen

[57] ABSTRACT

Certain propoxylate ethers, block copolymers and one ester has been found to be miticidal. Some members of this group also exhibit pediculicidal and/or ovicidal activity.

11 Claims, No Drawings

PROPOXYLATE TOXICANTS

BACKGROUND OF THE INVENTION

A great number of insecticidal toxicants are known today. However, because of increased concern about the overall safety of some of the known ectoparasitic toxicants, the search for new, safe and effective materials has intensified recently.

There are very few good toxicants against the scabies mite or itch mite. The female of the species burrows into the skin of the host and lays eggs within the burrow. An intense itching and rash develops in about a month. Serious and fatal infections are not uncommon in untreated animals. The majority of common insecticides are of little value as miticidal agents on the skin, and there is also a need for better agricultural miticides.

It is the object of this invention to provide new miticidal toxicants and compositions containing such toxicants. This and other objects of the invention will become apparent to those skilled in the art from the following detailed description.

SUMMARY OF THE INVENTION

This invention relates to the use of certain propoxylate derivatives as miticidal toxicants and to compositions containing those derivatives. More particularly, it has been found that certain propoxylate ethers, block copolymers and one ester exhibits miticidal activity. A few members of this group also exhibit pediculicidal and/or ovicidal activity.

DESCRIPTION OF THE INVENTION

The toxicants of the present invention are certain propoxylate derivatives, namely certain ethers, block copolymers and one ester. Other propoxylate derivatives including the propoxylate alcohols which have been studied have not been found to be effective. In referring to the compounds of this invention, the indication PPG followed by a number in parenthesis represents the number of repeating propoxy groups therein.

Of the propoxylated esters tested, only PPG (2) dibenzoate having the structure

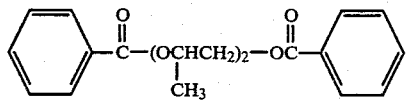

had miticidal activity.

Propoxylated ethers of the formula

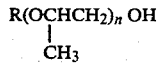

in which R is an alkyl group of 1 to 18 carbon atoms and n is a number such that the propoxy groups constitute about 40–90% of the ether have been found active. Preferably, the alkyl group contains 1–13 carbon atoms and the propoxy groups are at least 60 weight % of the ether.

Also found effective as miticidal toxicants are those propoxylate block copolymers of the formula

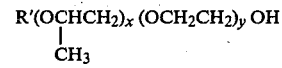

wherein R' is an alkyl group of 4 to 18 carbon atoms, x is a number such that the propoxy groups constitute about 20–45% of the copolymer and y is at least 1. In the preferred species of these copolymers, x is about 2–12 and y is about 3–50.

As will be shown in the Tables later, several of the ethers also exhibited a strong pediculicidal activity. These derivatives were PPG (3) myristyl ether, PPG (5) and PPG (9) butyl ether and PPG (10) cetyl ether. The PPG (5) and PPG (40) butyl ethers, the PPG (10) cetyl ether and PPG (10) cetyl ether phosphate exhibited good ovicidal activity. It has been observed that terminating the chain of the ether or block copolymer with a phosphate moiety enhanced miticidal activity.

Active toxicant compositions containing one or a mixture of the toxic propoxalate derivatives can be in the form of a liquid, powder, lotion, cream, gel or aerosol spray, or foam as the result of formulation with inert pharmaceutically or agriculturally acceptable carriers by procedures well known in the art. Any pharmaceutically or agriculturally acceptable carrier, whether aqueous or non-aqueous, which is inert to the active toxicant can be employed. By inert is meant that the carrier does not have a substantial detrimental effect on the miticidal, insecticidal or ovicidal toxicant activity of the active ingredient.

The active propoxylate derivatives are incorporated into the toxicant composition used to treat the animal, human, or environmental area host in need of such treatment, believed to be in need of such treatment, or desired to be prophylactically protected in an effective toxic amount. By such amount is meant the amount which will cause at least 50% mortality of the ectoparasites within 24 hours in the case of mites or lice and within two weeks in the case of ova in the testing protocols described below. The minimum concentration of propoxy derivative required to provide an effective toxic amount varies considerably depending on the particular derivative, the particular inert pharmaceutically acceptable carrier being employed and any other ingredients which are present. Thus, in one case a 2% concentration may suffice, while in other cases concentrations as high as 50 or 60% may be required to obtain an effective toxic dose. Usually, the derivatives will be present in concentrations of about 1 to 25%, and most preferably in concentrations of about 2–20%.

The instant toxicants can also be employed as an adjunct toxicant in a preparation which otherwise exhibits insecticidal and/or ovicidal activity. In such preparations, the term "effective toxic dose" means an amount which will increase the mortality rate by at least about 20%.

The testing protocols referred to above are as follows:

Miticidal Activity: Into a 1 cubic foot chamber held at room temperature is placed a covered microscope depression slide containing ten adult mixed sex mites, *Psoroptes equi* var. cuniculi. The slide is positioned at a distance of 10" horizontally and 4" below the tip of a mechanical spray device, and uncovered. The mechanical pump spray device delivered 50 milligrams of sample per depression of the actuator. The sample to be tested, maintained at room temperature, is shaken until homogeneous and placed in the mechanical pump spray device. The primed pump is depressed twice, releasing 100 milligrams of spray mist into the closed chamber. The mist is allowed to settle and the slide containing the mites is removed and covered. This point of time is considered zero hours. The covered slide is then held at room temperature, for 24 hours and microscopic observations are noted at 0, 1, 3, and 24 hours post-treatment. Controls are run in an identical manner as that described using water or the diluting agent, and net mortality results are reported.

Pediculicidal Activity: A 50 ml beaker is filled with tap water and allowed to come to room temperature (about 24° C.). Ten young adult male and ten young adult female lice (*Pediculus humanus corporis*) of the same age group and from the same stock colony are placed on a 2×2 cm coarse mesh patch. The sample to be tested, maintained at room temperature, is shaken until homogeneous and placed into a 50 ml beaker. The mesh patch is placed into the sample immediately after pouring, allowed to submerge, and after two minutes is removed and immediately plunged into the beaker containing the tap water. The patch is vigorously agitated every ten seconds and after one minute, the patch is removed and placed on paper toweling. The lice are then transferred to a 4×4 cm black corduroy cloth patch and this point in time is considered zero hours. Thereafter the corduroy patch is placed in a petri dish which is covered and stored in a 30° C. holding chamber.

Ovicidal Activity: 15 adult, 5 to 10 day old, female lice (*Pediculus humanus corporis*) are placed on a 2×2 cm nylon mesh patch which is placed in a petri dish, covered and maintained in an incubator at 30° C. for 24 hours. The adult lice are then removed and the number of plump, viable eggs and shrivelled nonfertile eggs on a patch are recorded. The sample to be tested, maintained at room temperature, is shaken until homogeneous and poured into a 50 ml beaker. Immediately after the pouring, the mesh patch is placed into the beaker, allowed to submerge, and after two minutes is removed and immediately plunged into a 50 ml beaker containing tap water at room temperature (about 24° C.). The batch is vigorously agitated every ten seconds and after one minute, the batch is removed and placed on paper toweling for one minute. The patch is then placed in a petri dish which is covered and stored in the 30° C. incubator. Fourteen days following treatment, the number of hatched eggs and the number of shriveled or unhatched eggs is noted.

In all three protocols, controls are run in identical manner to that described with room temperature (24° C.) tap water substituted for the sample to be tested. The results of these tests are reported as net results.

The miticidal, pediculicidal and ovicidal activity of various toxicants of the instant invention and of related compounds were determined in the test protocols described above. The concentration of the material which caused 50% mortality ($LC_{50}$) was determined in a system where the material was mixed with isopropanol for determining miticidal activity and with 25% isopropanol and water q.s. for pediculicidal and ovicidal activity. In the following Tables, an asterisk (*) means that the $LC_{50}$ was greater than 70% (the maximum concentration tested). The results are shown in the following Tables.

Table 1

Propoxylate Alcohols
$$H(OCH_2CH)_nOH$$
$$|$$
$$CH_3$$

| n | Miticidal | Pediculicidal | Ovicidal |
|---|---|---|---|
| 9 | * | * | * |
| 12 | * | * | * |
| 17 | * | * | * |
| 20 | * | * | * |

Table 2

Propoxylate Esters

| Compound | Pediculicidal | Ovicidal | Miticidal |
|---|---|---|---|
| PPG (2) dibenzoate | * | * | 28 |
| PPG (26) oleate | * | * | * |
| PPG (36) oleate | * | * | * |

Table 3

Propoxylate Ethers of the formula $R(OCHCH_2)nOH$
$$|$$
$$CH_3$$

| | | $LC_{50}$, % | | |
|---|---|---|---|---|
| | Wt. % PPG | Pediculicidal | Ovicidal | Miticidal |
| PPG (2) methyl ether | 78.4 | * | * | 6.4 |
| PPG (2) lanolin ether + | 21.4 | * | * | * |
| PPG (3) methyl ether | 84.5 | * | * | 1.1 |
| PPG (3) myristal ether | 44.8 | 2.8 | 56 | 1.9 |
| PPG (5) butyl ether | 79.7 | 23 | 9.5 | 4.8 |
| PPG (5) lanolin ether + | 40.5 | * | * | * |
| PPG (9) butyl ether | 87.6 | 9 | * | 24 |
| PPG (10) methyl glucose ether | 74.9 | * | * | * |
| PPG (10) cetyl ether | 70.6 | 15 | 20.5 | 54 |
| PPG (10) cetyl ether phosphate | 64.2 | * | 27 | 20 |
| PPG (10) oleyl ether | 62.1 | * | 56 | 24 |
| PPG (10) lanolin ether + | 57.7 | * | * | * |
| PPG (11) stearyl ether | 64.2 | * | * | 45 |
| PPG (15) stearyl ether | 76.3 | 53 | 56 | 37 |
| PPG (18) butyl ether | 93.4 | * | 50.5 | * |
| PPG (20) methyl glucose ether | 85.7 | * | * | * |
| PPG (20) lanolin ether + | 73.1 | * | * | * |
| PPG (23) oleyl ether | 83.3 | * | * | * |
| PPG (30) cetyl ether | 87.8 | * | * | 58 |
| PPG (30) oleyl ether | 86.7 | * | * | * |
| PPG (30) lanolin ether + | 80.3 | * | * | 58 |
| PPG (40) butyl ether | 96.9 | * | 38 | * |
| PPG (50) cetyl ether | 92.3 | * | * | * |
| PPG (50) oleyl ether | 89.1 | * | * | * |

Table 4

Block copolymers of the formula
$$R'(OCHCH_2)_x (OCH_2CH_2)_y OH$$
$$|$$
$$CH_3$$

| | | | | $LC_{50}$, % | | |
|---|---|---|---|---|---|---|
| R' | Wt. % PPG | x | y | Pediculicidal | Ovicidal | Miticidal |
| Butyl | 36 | 2 | 3 | * | * | 2 |
| Myristyl | 44.8 | 3 | 3 | * | * | 7.5 |
| Butyl | 43.1 | 5 | 7 | * | * | 6.5 |
| Cetyl phosphate | 27.5 | 5 | 10 | * | 67 | 3.3 |

Table 4-continued

Block copolymers of the formula
$$R'(OCHCH_2)_x (OCH_2CH_2)_y OH$$
$$\phantom{R'(O}|\phantom{CHCH_2)_x (OCH_2CH_2)_y OH}$$
$$\phantom{R'(O}CH_3$$

| R' | Wt. % PPG | x | y | LC$_{50}$, % Pediculicidal | Ovicidal | Miticidal |
|---|---|---|---|---|---|---|
| Cetyl | 20.5 | 5 | 20 | * | * | 14 |
| 12 to 18 carbon chain blend | ≧31.6 ≦34.2 | 6 | 11 | * | * | 10 |
| Butyl | 46.4 | 9 | 12 | * | * | * |
| Cetyl and Stearyl blend | ≧33.5 ≦34.1 | 10 | 20 | * | * | 18 |
| Lanolin + | 21 | 12 | 50 | * | * | 11 |
| Glyceryl | 54.8 | 24 | 24 | * | * | * |
| Glyceryl | 86.1 | 66 | 12 | * | * | * |

+ Calculated using Lanestrol as the alkyl group.

The following Table 5 shows the use of the toxicant in an adjunctive capacity:

Table 5

| | % W/W | % Mortality Pediculicidal | Miticidal |
|---|---|---|---|
| Isopropyl alcohol | 25 | | |
| Stearamine oxide | 10 | 100 | 0 |
| Cocoyl sarcosine | 1 | | |
| Water | 64 | | |
| PPG (2) methyl ether | 15 | | |
| Isopropyl alcohol | 25 | | |
| Stearamine oxide | 10 | 100 | 100 |
| Cocoyl sarcosine | 1 | | |
| Water | 49 | | |

The PPG (2) methyl ether has also been tested against *Bryobia praetiosa*, a mite of agricultural importance as follows: A 1% concentration was prepared in ethanol diluted with deionized water to an ethanol content of less than 50%. A control sample was prepared containing 50% ethanol and 50% water. Twenty five mites were placed in each of two glass Petri dishes ringed with vaseline. The test sample was placed in an 8-dram vial, weighed and placed in a Presto spray unit. The spray unit was centered 32.5 cm from the open end of a large bell jar and the test mites were placed 62.5 cm from the spray unit. A 2 second burst of spray (1.02 grams) was directed into the chamber, the spray allowed to settle, the Petri dish removed, and morbidity/mortality counts were recorded at 5, 10, 15 and 60 minutes. A final count was recorded at 24 hours. The treated mites and controls were held at about 27° C. and 80% relative humidity. The results are shown in Table 6.

Table 6

| | Morbidity 5 min. | 10 min. | 15 min. | 1 hr. | Mortality 24 hrs. |
|---|---|---|---|---|---|
| PPG (2) methyl ether | 68% | 68% | 68% | 72% | 52% |
| Control | 4% | 4% | 4% | 4% | 4% |

As noted above, various end use formulations can be prepared. Some typical formulations are set forth below and the amounts recited are percentages by weight:

| | % W/W |
|---|---|
| Pediculicidal and Miticidal Stick | |
| PPG (3) myristyl ether | 25.0 |

-continued

| | % W/W |
|---|---|
| Sodium stearate | 8.0 |
| Sorbital | 3.5 |
| Ethanol | 54.0 |
| Water | 9.5 |
| Miticidal Lotion | |
| PPG (3) methyl ether | 2 |
| Glyceryl monostearate | 5 |
| Polysorbate 60 | 2 |
| Isopropanol | 25 |
| Water | 66 |
| Miticidal Lotion | |
| PPG (2) POE (3) butyl ether | 1 |
| Glyceryl monostearate | 4 |
| Polysorbate 60 | 2 |
| Isopropanol | 25 |
| Water | 68 |
| Liquid pediculicide suitable for mechanical spray application or inunction | |
| PPG (3) myristyl ether | 25 |
| Isopropanol | 25 |
| Water | 50 |
| Ovicidal Gel | |
| PPG (5) butyl ether | 30 |
| Isopropanol | 10 |
| Polysorbate 60 | 3 |
| Carboxypolymethylene | 1 |
| Triethanolamine | 2 |
| Water | 54 |
| Pediculicidal Cream | |
| PPG (10) cetyl ether | 30.0 |
| Glyceryl monostearate | 21.0 |
| Isopropanol | 25.0 |
| Polysorbate 60 | 3.5 |
| Sorbitan monostearate | 1.5 |
| Water | 19.0 |
| Pediculicidal and miticidal quick breaking aerosol foam | |
| PPG (3) myristyl ether | 25 |
| Isopropanol | 25 |
| Mono and diglycerides of edible fats | 8 |
| Glycerine | 3 |
| Water | 31 |
| Isobutane | 8 |
| Miticidal aerosol spray | |
| PPG (2) methyl ether | 10 |
| Isopropanol | 15 |
| Isobutane | 15 |
| Water | 37 |
| Miticidal Lotion | |
| PPG (2) methyl ether | 5 |
| Water | 95 |
| Miticidal aerosol spray | |
| PPG (3) methyl ether | 3 |
| Water | 89 |

| | % W/W |
|---|---|
| Isobutane | 8 |

Various changes and modifications can be made in the present invention without departing from the spirit and scope thereof. The various embodiments described herein were for the purpose of illustration only and were not intended to limit the invention. Unless otherwise specified, all temperatures have been in degrees Centigrade and all parts and percentages by weight throughout this specification and claims.

We claim:

1. A method of controlling ectoparasites or their ova which comprises applying to a host in need of such control an effective toxic amount of at least one polyoxypropylene glycol derivative selected from the group consisting of; ethers of the formula

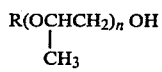

wherein R is a 1 to 18 carbon atom alkyl group and n is a number such that the propoxy groups constitute 40 to 90% of said ether and the phosphates of said ethers.

2. The method of claim 1 wherein R is a 1 to 13 carbon atom alkyl group and n is a number such that the propoxy groups constitute at least about 60% of said ether.

3. A method according to claim 2 wherein said ether is selected from the group consisting of polyoxypropylene glycol (2) methyl ether, polyoxypropylene glycol (3) methyl ether, polyoxypropylene glycol (9) butyl ether, polyoxypropylene (10) cetyl ether phosphate and polyoxypropylene glycol (10) oleyl ether.

4. The method of claim 1 wherein said derivative is polyoxypropylene glycol (3) myristyl ether.

5. The method of claim 1 wherein said derivative is polyoxypropylene glycol (5) butyl ether.

6. The method of claim 1 wherein said derivative is employed in combination with an inert pharmaceutically or agriculturally acceptable carrier.

7. The method of claim 6 wherein the carrier is aqueous.

8. A method of controlling mites which comprises applying to a host in need of such control an effective toxic amount of at least one polyoxypropylene glycol derivative selected from the group consisting of ethers of the formula

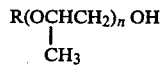

wherein R is a 1 to 18 carbon atom alkyl group and n is a number such that the propoxy groups constitute 40 to 90% of said ether and the phosphates of said ethers.

9. The method of claim 8 wherein R is a 1 to 13 carbon atom alkyl group and n is a number such that the propoxy groups constitute at least about 60% of said ether.

10. The method of claim 9 wherein said ether is selected from the group consisting of polyoxypropylene glycol (2) methyl ether, polyoxypropylene glycol (3) methyl ether, polyoxypropylene glycol (9) butyl ether, polyoxypropylene (10) cetyl ether phosphate, polyoxypropylene glycol (10) olely ether, polyoxypropylene glycol (3) myristyl ether and polyoxypropylene glycol (5) butyl ether.

11. The method of claim 8 wherein said derivative is employed in combination with an inert agriculturally acceptable carrier.